United States Patent [19]

Inoue et al.

[11] 4,356,331
[45] Oct. 26, 1982

[54] PROCESS FOR SEPARATING AN ALKYLPHENOL ISOMER

[75] Inventors: Takehisa Inoue, Tokyo; Kishio Miwa, Kamakura, both of Japan

[73] Assignee: Toray Industries, Incorporated, Japan

[21] Appl. No.: 186,480

[22] Filed: Sep. 12, 1980

[30] Foreign Application Priority Data

Sep. 20, 1979 [JP] Japan ................. 54-120085

[51] Int. Cl.³ ............. C07C 37/82; C07C 37/70
[52] U.S. Cl. ........................ 568/758; 568/750
[58] Field of Search ........... 568/758, 750, 751, 752

[56] References Cited

U.S. PATENT DOCUMENTS

| 3,014,073 | 12/1961 | Fleck | 568/750 |
| 3,442,958 | 5/1969 | Choo | 568/758 |
| 3,969,422 | 7/1976 | Neuzil | 568/750 |
| 4,124,770 | 11/1978 | Miyake et al. | 568/758 |

Primary Examiner—Werren B. Lone
Attorney, Agent, or Firm—Scully, Scott, Murphy & Presser

[57] ABSTRACT

A feed containing a mixture of at least two alkylphenol isomers is contacted with a zeolite adsorbent to allow an alkylphenol isomer in the mixture to be selectively adsorbed on the adsorbent, and then the adsorbent is contacted with an aliphatic ketone desorbent to desorb the adsorbed isomer.

12 Claims, 2 Drawing Figures

PROCESS FOR SEPARATING AN ALKYLPHENOL ISOMER

BACKGROUND OF THE INVENTION

This invention relates to a process for separating an alkylphenol isomer and more particularly to the improvement of a desorbent in the separation of an alkylphenol isomer from a feed containing a mixture of alkylphenol isomers by adsorptive separation techniques using a zeolite adsorbent and the desorbent.

That an alkylphenol isomer can be separated using zeolite adsorbents is well known from Japanese Patent Publication No. 5155/62, Japanese Patent Laying Open Prints Nos. 26831/76, 108025/76 and 93725/77, etc. As the desorbent used in such separating operation, phenols and alcohols are known.

It is an object of this invention to provide desorbents capable of being used effectively when selectively adsorbing an alkylphenol isomer from a feed containing a mixture of alkylphenol isomers using a zeolite adsorbent.

It is another object of this invention to provide a process for separating an alkylphenol isomer using a new desorbent which exhibits a remarkable effect in the separation and recovery of an alkylphenol isomer from a mixture of alkylphenol isomers continuously while repeating adsorption and desorption steps alternately.

Other objects and advantages of this invention will become apparent from the following description.

SUMMARY OF THE INVENTION

The foregoing objects of this invention can be attained by using a desorbent comprising an aliphatic ketone in the selective separation of an alkylphenol isomer from a feed containing a mixture of alkylphenol isomers using a zeolite adsorbent.

More preferably, the foregoing objects of this invention can be achieved by using a desorbent comprising an aliphatic ketone and an aliphatic alcohol in the selective separation of an alkylphenol isomer from a feed containing a mixture of alkylphenol isomers using a zeolite adsorbent.

DETAILED DESCRIPTION OF THE INVENTION

Figure 1:
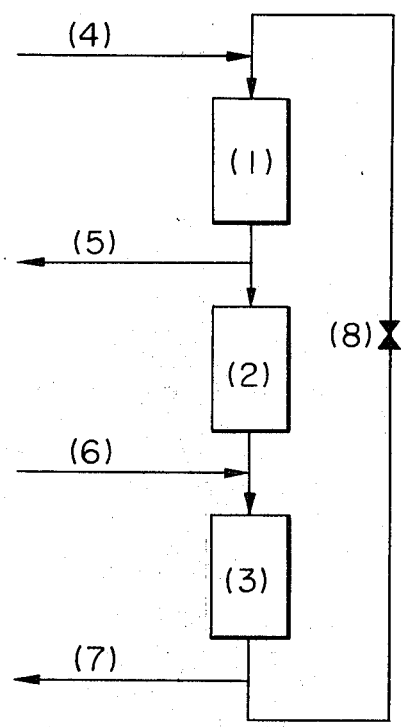

Fundamental operations for separating an alkylphenol isomer from a mixture of alkylphenol isomers by continuous adsorptive separation techniques comprise the following adsorption and desorption steps.

(1) In the adsorption step, a feed containing a mixture of alkylphenol isomers is contacted with an adsorbent which has been subjected to the desorption step as will be referred to in (2) below, whereby a more easily adsorptive component in the feed is selectively adsorbed while expelling a part of the desorbent which remains in the adsorbent. At the same time a less selective adsorbed component in the feed is recovered as a raffinate stream together with the desorbent.

(2) In the desorption step, the selectively adsorbed component is expelled from the adsorbent by the desorbent and is recovered as an extract stream.

As will be apparent from the above description, the desorbent used in the adsorptive separation process should have the function of expelling the selectively adsorbed component from the adsorbent in the desorption step, and it goes without saying that the desorbent itself must be expelled in the following adsorption step by the more easily selectively adsorbed component in the feed to allow the adsorbent to be used continuously in a recyclic manner.

In addition, a more important characteristic required of desorbents is that they should be effective in increasing the adsorptive selectivity among alkylphenol isomers. That is, the adsorption and desorption steps for adsorptive separation for a mixture of alkylphenol isomers are carried out always in the presence of a desorbent, so if the adsorptive selectivity among alkylphenol isomers is increased by the desorbent, the adsorptive separation can be effected more efficiently. The adsorptive selectivity among alkylphenol isomers may be expressed by a selectivity value, $\alpha$, according to the following equation (1):

$$\alpha_{A/B} = \frac{\left(\frac{\text{wt. percent of } A \text{ in adsorbed phase}}{\text{wt. percent of } B \text{ in adsorbed phase}}\right)}{\left(\frac{\text{wt. percent of } A \text{ in unadsorbed phase}}{\text{wt. percent of } B \text{ in unadsorbed phase}}\right)} \quad (1)$$

If a selectively adsorbed component, e.g. p-cresol, among cresol isomers is taken to be A and a component difficult to be adsorbed, e.g. m-cresol, is B, the $\alpha_{A/B}$ is preferably as high as possible. A low $\alpha_{A/B}$ requires a large amount of adsorbent in the adsorptive separation of a cresol isomer, decreases the recovery of the object component per unit adsorbent and increases the energy cost. Thus a low $\alpha_{A/B}$ is not only uneconomical but also it sometimes makes it impossible to obtain the object component at a desired purity. Therefore, it is very important to select such a desorbent that a high separation efficiency is attained in the presence thereof, in other words, the $\alpha_{A/B}$ measured in the presence thereof gives a higher value.

As previously noted, moreover, the desorbent must be able to expel in the desorption step a selectively adsorbed component on the adsorbent, e.g. p-cresol, and the desorbent itself which was adsorbed on the adsorbent in the desorption step must be capable of being expelled in the adsorption step by an easily selectively adsorbed component in the feed, e.g. p-cresol, to allow the adsorbent to be used continuously in a recyclic manner. In other words, it is desirable that the desorbent and the selectively adsorbed component, e.g. p-cresol, resemble closely in the adsorptive power; that is, a desirable desorbent is such that in the following equation the selectivity value of the selectively adsorbed component A for the desorbent, $\alpha_{A/D}$, be as close to unity as possible:

$$\alpha_{A/D} = \frac{\left(\frac{\text{wt. percent of } A \text{ in adsorbed phase}}{\text{wt. percent of desorbent in adsorbed phase}}\right)}{\left(\frac{\text{wt. percent of } A \text{ in unadsorbed phase}}{\text{wt. percent of desorbent in unadsorbed phase}}\right)} \quad (2)$$

A larger $\alpha_{A/B}$ than unity would require a large amount of desorbent for expelling the selectively adsorbed component from the adsorbent in the desorption step, lower the concentration of the selectively adsorbed component in the extract and cause an increase in energy cost for recovering the selectively adsorbed component from the extract by distillation, and thus is uneconomical. If the $\alpha_{A/D}$ is close to zero, the desorbent becomes difficult to be displaced by a selectively adsorbed components in the adsorption step, allowing a larger amount of desorbent to occupy the selective adsorption pores of zeolite, with the result that the separation performance for an alkylphenol isomer is deteriorated.

It goes without saying that desirable desorbents should be capable of being separated from cresol easily by the conventional distillation separation technique and be chemically stable.

The desorbents of this invention satisfy all of the above-mentioned characteristics required of a desorbent, and are superior to alcohols which have heretofore been considered to be the best.

The desorbents of this invention comprise an aliphatic ketone. As the aliphatic ketone, dialkyl ketones represented by the formula $R_1-CO-R_2$ wherein $R_1$ and $R_2$ are each an alkyl group of $C_1$ to $C_3$ are preferred, among which diethyl ketone, methyl-n-propyl ketone and methyl-iso-propyl ketone are particularly preferred. Such aliphatic ketones may be used alone as a desorbent, or in combination with other desorbent, and they may be used in a diluted condition with a diluent such as a paraffin, a cycloparaffin or an aromatic hydrocarbon. Particularly, desorbents comprising an aliphatic ketone and an aliphatic alcohol afford a synergistic effect which in their single use cannot be attained. As the aliphatic alcohol, straight chain alcohols of $C_4$ to $C_6$ such as n-butanol, n-pentanol and n-hexanol are especially preferred.

The blending ratio of alcohol to ketone is not limited, but preferably it is in the range of from 1:20 to 20:1 and more preferably from 1:5 to 5:1. But the optimum ratio should be decided by the characteristics of the zeolite adsorbent used.

By way of illustrating the mixture of alkylphenol isomers fed in the process of this invention, mention may be made of a mixture containing at least two cresol isomers selected from para-cresol, meta-cresol and ortho-cresol, and a mixture containing at least two ethylphenol isomers selected from para-ethylphenol, meta-ethylphenol and ortho-ethylphenol. Particularly preferred is a mixture which contains para-cresol as the essential component and further contains meta- and/or ortho-cresol.

As the adsorbent used in the process of this invention, any zeolite adsorbents are employable, but preferably used are those having the ability to selectively adsorb p-cresol or p-alkylphenol, for example, faujasite type zeolites containing one or more cations selected from Groups IA and IIA metals, among which potassium-containing faujasite is preferred. Those containing two kinds of cations such as potassium-strontium and potassium-barium are particularly preferred.

The adsorptive separation process of this invention is carried out at a temperature in the range of from 0° to 350° C., preferably from room temperature to 250° C., and at a pressure in the range of from atmospheric pressure to 40 kg/cm², preferably from about atmospheric pressure to 30 kg/cm².

The adsorptive separation process of the invention may be practised in both vapor and liquid phases, but it is preferable to utilize liquid phase separation at a low temperature in order to suppress the undesired side reaction of the feed or desorbent.

In the adsorptive separation for a mixture of alkylphenol isomers according to the process of this invention, if cresol which has been prepared by the so-called cymene process is used as the starting material, it is possible to separate and recover a high purity p-cresol from the extract and a high purity m-cresol from the raffinate, since o-cresol is little contained in the said starting material. In case the starting mixture of alkylphenol isomers contain three or more isomers or other impurities, the decision whether the substance having a medium adsorptive power is to be led to the extract side or to the raffinate side depends on which of the substance having the strongest adsorptive power and the substance having the weakest adsorptive power is to be separated and recovered as product.

Referring to the drawings:

FIG. 1 represents a schematic arrangement and flow diagram illustrating one specific embodiment of this invention, showing a fixed bed apparatus connected for countercurrent flow operations. This drawing is intended to be illustrative, and not to define or to limit the scope of the invention, which is defined in the claims.

Referring to the specific embodiment selected for illustration, which will be described in specific terms hereinafter without intending to limit the scope of the invention thereby, the apparatus comprises three zones, 1 being a desorption zone, 2 being a rectification zone, and 3 being an adsorption zone.

In the desorption zone, a selectively adsorbed component on an adsorbent is displaced by a desorbent and flows out together with the desorbent. A portion of the stream containing the adsorbate which has flowed out of the desorption zone is taken out of the system as a product stream of the adsorbate, while the remaining portion is fed as a reflux to the rectification zone. In the rectification zone, the said reflux is contacted countercurrentwise with an apparent stream of the adsorbent to improve the purity of product. In the adsorption zone, the adsorbent is selectively adsorbed from the starting mixture, while the raffinate stream containing the desorbent is taken out. The desorption, rectification and adsorption zones are each composed of plural adsorption chambers charged with a zeolite adsorbent, the adsorption chambers being interconnected through an open/close valve with the flow between the adsorption and desorption zones being closed.

In operation, while a valve (8) is opened, a desorbent feed line (4), an extract withdrawal line (5), a starting mixture feed line (6) and a raffinate withdrawal line (7) are moved in the direction of the fluid flow along the adsorption chambers at predetermined time intervals whereby in appearance the top adsorption chambers in the rectification, adsorption and desorption zones are transferred to the bottoms of the desorption, rectification and adsorption zones respectively to create an apparent adsorbent stream, thus permitting a continuous separation for the feed.

Figure 2:
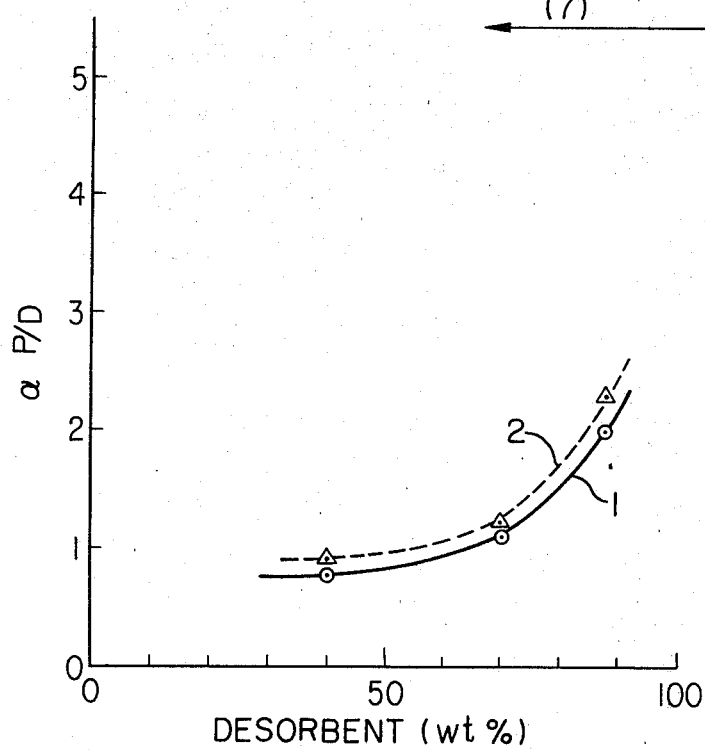

FIG. 2 graphically shows the relation between the desorbent concentration and $\alpha_{p/D}$ (p being para-cresol) in the case of Sr-K-Y type zeolite as an adsorbent and diethyl ketone (1), n-butanol (2) each individually as a desorbent, in which (1),(2) are plotted results of values at the measuring temperature of 130° C. From the graph of FIG. 2 it is seen that as the desorbent concentration becomes high the $\alpha_{p/D}$ value becomes high as well. Since in the desorption step p-cresol is expelled by a desorbent, the $\alpha_{p/D}$ value especially in the high desorbent concentration region is important and it can be regarded as an important factor in determining the performance of desorbent. This is because the p-cresol concentration the adsorbent in the desorption step ranges from a relatively low concentration to a substantially zero region.

To further illustrate this invention, and not by way of lilitation, the following examples are given.

EXAMPLE 1

Sodium type Y zeolite was subjected to ion exchange treatment using potassium nitrate so that not less than 90% of the sodium ions were ion-exchanged with potassium, then the zeolite was calcined at 500° C. for 3 hours to prepare a K-Y type adsorbent. Then, 2 g. of the said adsorbent and 2 g. of a liquid-phase mixture consisting of an aliphatic ketone as the desorbent and a mixture of cresol isomers were charged into an autoclave having a 5 ml. content volume, then allowed to stand for 1 hour at 80° C. while stirring was applied at times. The composition of the fed liquid-phase mixture was desorbent- :para-cresol:meta-cresol:ortho-cresol=4:2:2:2 (in weight ratio). The composition of the liquid-phase mixture after contact with the adsorbent was analyzed by gas chromatography, and $\alpha_{A/B}$ values in the foregoing equation (1) were calculated, the results of which are set out in Table 1 below.

TABLE 1

| Desorbent | Selectivity Value | | |
|---|---|---|---|
| | $\alpha_{p/m}$ | $\alpha_{p/o}$ | $\alpha_{p/DES}$ |
| Diethyl ketone | 2.7 | 4.3 | 1.8 |
| Methyl-isopropyl ketone | 3.4 | 6.0 | 2.0 |
| Methyl-n-propyl ketone | 2.5 | 4.1 | 1.8 |
| Non | 1.8 | 2.2 | — |

In the above table, p ... para-cresol, m ... meta-cresol, o ... ortho-cresol, DES .. desorbent.

From the above results it is understood that the desorbent of this invention is remarkably superior in the adsorptive selectivity for para-cresol as compared with the other isomers and is also superior in the selectivity between meta-cresol and ortho-cresol. Furthermore, that the selectivity value of para-cresol for desorbent approaches unity indicates that the desorbent of this invention is a particularly preferable desorbent for the continuous operation referred to hereinbefore. Thus, from the above results it is seen that the desorbent of this invention has unprecedentedly well-balanced characteristics.

EXAMPLE 2

Experiment was made using the continuous adsorptive separator shown in FIG. 1. In this apparatus, adsorption chambers each having a content volume of 19.3 cc and charged with the same K-Y type zeolite (24-42 mesh) as that used in Example 1 were disposed 4, 6 and 6 in the desorption, rectification and adsorption zones, respectively. The operation for adsorptive separation was effected by a time-actuated automatic control apparatus, and the shift interval was programmed for 1.8 minutes.

From the starting mixture feed line a mixture of cresol isomers at the ratio of p-cresol to m-cresol of 38:62 (in weight ratio), which had been preheated to 100° C., was fed continuously at the flow rate of 41 cc/hr. From the desorbent feed line, diethyl ketone preheated to 100° C. was continuously fed at the flow rate of 560 cc/hr, and from the extract withdrawal line there was withdrawn p-cresol together with diethyl ketone at the flow rate of 92 cc/hr. Further, from the raffinate withdrawal line, m-cresol containing diethyl ketone was withdrawn at the flow rate of 509 cc/hr.

Separating the two by distillation and removing diethyl ketone left m-cresol of 99.5 wt.% purity and p-cresol of 99.3 wt.% purity.

EXAMPLE 3

Sodium type Y zeolite (Na-Y) was subjected to ion exchange treatment using potassium nitrate so that not less than 90% of the sodium ions were ion-exchanged with potassium, and calcined at 500° C. for 3 hours to prepare a potassium type Y zeolite (K-Y), then 100 g. of the so-prepared adsorbent was immersed in 300 g. of a 3 wt.% strontium nitrate solution and ion-exchanged at 90° C. for 1 hour, then further calcined at 500° C. for 1 hour to prepare Sr-K-Y zeolite.

2 g. of the adsorbent thus obtained and 2 g. of a liquid-phase mixture consisting of a desorbent and a mixture of cresol isomers were charged into an autoclave having a 5 ml. content volume, then allowed to stand for 1 hour at 80° C. The composition of the fed liquid-phase mixture was desorbent:p-cresol:m-cresol:decalin=4:3:3:1 (in weight ratio), in which decalin was added as a standard substance in gas chromatography, it being a substantially unadsorbed component.

As the desorbent there were used diethyl ketone, n-butyl alcohol and an equal weight mixture of both. The composition of the liquid-phase mixture after contact with the adsorbent was analyzed, and $\alpha_{p/m}$ values were calculated from the amount of change in composition of the liquid-phase mixture, the results of which are shown in Table 2.

EXAMPLE 4

Experiment was made under the same conditions as in Example 3 except that as the adsorbent there was used the potassium Y zeolite before ion-exchange with strontium nitrate as shown in Example 3. The results of the experiment are set out also in Table 2.

EXAMPLE 5

100 g. of the potassium Y zeolite referred to in Example 4 was immersed in 300 g. of a 3.7 wt.% barium nitrate solution and ion-exchanged at 90° C. for 1 hour, then calcined at 500° C. for 1 hour to prepare Ba-K-Y zeolite. Using this zeolite there was made experiment under the same conditions as in Example 3, the results of which are set out also in Table 2.

From Examples 3 through 5 it is seen that the $\alpha_{p/m}$ in the presence of a desorbent is improved in the combination of alcohol and ketone as a mixed desorbent rather than in either of the two alone, and that the mixed desorbent exhibits a synergistic effect. And this effect is more distinguished in Sr-K-Y or Ba-K-Y than in K-Y.

TABLE 2

| | | $\alpha_{p/m}$ | | |
|---|---|---|---|---|
| | Example No. | 3 | 4 | 5 |
| | Adsorbent | Sr-K-Y | K-Y | Ba-K-Y |
| Desorbent | diethyl ketone | 3.21 | 2.67 | 2.56 |
| | n-butyl alcohol | 2.50 | 2.24 | 2.38 |
| | n-butyl alcohol + diethyl ketone | 5.31 | 3.01 | 3.48 |

EXAMPLE 6

The selectivity value $\alpha_{p/D}$ in the region where the desorbent concentration approaches 100% was calculated from the retention time of tracer according to the dynamic pulse method using an adsorbent packed bed 5 mm in inside dia. by 120 cm long. In the fluid inlet portion of the said packed bed there was mounted a tracer injecting changeover valve having a capacity of 200 μl, and in the outlet portion thereof was mounted a refractometer for monitoring the efflux curve of the injected tracer. The packed bed was placed in a constant temperature bath.

As the experiment procedure, while passing a desorbent as carrier through the said packed bed at a constant flow rate, first a substantially unadsorbed component (e.g. cyclohexane) is injected as a tracer and its retention time $t_c$ is measured, then tracer of p-cresol diluted to 10 wt.% with desorbent is injected and its retention time $t_p$ is measured. Since the desorbent itself is a carrier, its retention time $t_D$ can be calculated from the ratio of the total space volume including selective adsorption pores in the packed bed to the flow rate of carrier. From the above retention times there can be obtained $\alpha_{p/D}$ using the following equation as a general approach in the dynamic pulse method:

$$\alpha_{p/D} = \frac{t_p - t_c}{t_D - t_c}$$

The Sr-K-Y zeolite adsorbent referred to in Example 3 was used.

As the desorbent there were chosen diethyl ketone and n-butyl alcohol, and $\alpha_{p/D}$ values were measured in their uses alone and in combination. The adsorption temperature is 130° C. The results are shown in Table 3 below.

TABLE 3

| Desorbent Ratio n-C$_4$OH/(DEK + n-C$_4$OH) | Selectivity Value $\alpha_{p/D}$ |
| --- | --- |
| 0 | 3.0 |
| 0.25 | 2.0 |
| 0.5 | 2.4 |
| 0.75 | 2.5 |
| 1.0 | 3.7 |

From Table 3 it is seen that the desorbent comprising a mixture of an aliphatic ketone and an aliphatic alcohol exhibits a lower $\alpha_{p/D}$ value and that a synergistic effect is recognized in this mixed desorbent.

EXAMPLE 7

Experiment was made under the same conditions as in Example 6, in which experiment there were chosen diethyl ketone/n-amyl alcohol, methyl propyl ketone/n-butyl alcohol, and methyl propyl ketone/n-amyl alcohol, as mixed desorbents. The results of the experiment are set out in Tables 4 through 6, in all of which there is recognized a synergistic effect.

TABLE 4

| Desorbent Ratio n-C$_5$OH/(DEK + n-C$_5$OH) | Selectivity Value $\alpha_{p/D}$ |
| --- | --- |
| 0 | 3.1 |
| 0.3 | 2.2 |
| 0.7 | 2.7 |
| 1.0 | 4.0 |

TABLE 5

| n-C$_4$OH/(MPK + n-C$_4$OH) | $\alpha_{p/D}$ |
| --- | --- |
| 0 | 3.3 |
| 0.5 | 2.2 |

TABLE 5-continued

| n-C$_4$OH/(MPK + n-C$_4$OH) | $\alpha_{p/D}$ |
| --- | --- |
| 1.0 | 3.9 |

TABLE 6

| n-C$_5$OH/(MPK + n-C$_5$OH) | $\alpha_{p/D}$ |
| --- | --- |
| 0 | 3.4 |
| 0.5 | 2.3 |
| 1.0 | 4.0 |

We claim:

1. An adsorptive-separation process for a mixture of monoalkylphenol isomers selected from the group consisting essentially of a mixture containing at least two cresol isomers selected from para-cresol, meta-cresol and ortho-cresol, and a mixture containing at least two ethylphenol isomers selected from para-ethylphenol, meta-ethylphenol, and ortho ethylphenol, said process comprising:

(i) contacting a feed containing a mixture of monoalkylphenol isomers with a faujasite type Y zeolite containing potassium cations adsorbent; and (ii) contacting said faujasite type Y zeolite containing potassium cations adsorbent resulting from step (i) with a desorbent comprising an aliphatic ketone and an aliphatic alcohol, said aliphatic ketone having the formula $R_1$—CO—$R_2$, wherein $R_1$ and $R_2$ are each alkyl and wherein said contacting in steps (i) and (ii) is carried out at a temperature in the range of from 0° to 350° C. and at a pressure in the range of from atmospheric to 40 kg/cm$^2$.

2. The process as defined in claim 1, wherein $R_1$ and $R_2$ are the same or different alkyl group of $C_1$ to $C_3$.

3. The process as defined in claim 1, in which said aliphatic ketone is a member selected from the group consisting of diethyl ketone, methyl n-propyl ketone and methyl iso-propyl ketone.

4. The process as defined in claim 1, in which said aliphatic alcohol is a straight-chain aliphatic alcohol of $C_4$ to $C_6$.

5. The process as defined in claim 1, in which the weight ratio of said aliphatic ketone to said aliphatic alcohol is in the range of from 1:20 to 20:1.

6. The process as defined in claim 1, in which said monoalkylphenol isomers are cresol isomers.

7. The process as defined in claim 1 comprising the further steps of:

(iii) removing a mixture containing said desorbent and monoalkylphenol; and (iv) separating monoalkylphenol from said mixture.

8. The process as defined in claim 1 wherein said feed containing a mixture of monoalkylphenol isomers is selected from the group consisting of a mixture containing at least two cresol isomers selected from the group consisting of para-cresol, meta-cresol and ortho-cresol and a mixture containing at least two ethylphenol isomers selected from the group consisting of para-ethylphenol, meta-ethylphenol and ortho-ethylphenol.

9. The process as defined in claim 1 wherein said aliphatic ketone is diethyl ketone and said aliphatic alcohol is n-butyl alcohol.

10. A process for the separation of para-cresol from a feed containing a mixture of cresol isomers including para-cresol, said process comprising:

(a) passing said feed into contact with a faujasite type Y zeolite containing potassium cations adsorbent capable of selectively adsorbing para-cresol from said feed, at a temperature in the range of from 0° to 350° C. and at a pressure in the range of from atmospheric to 40 kg/cm$^2$, thereby adsorbing a greater percentage of para-cresol than other components of said feed on said adsorbent;

(b) desorbing para-cresol from said adsorbent by contacting said adsorbent with a desorbent comprising an aliphatic ketone and an aliphatic alcohol, said aliphatic ketone having the formula $R_1$—CO—$R_2$, wherein $R_1$ and $R_2$ are each alkyl;

(c) removing a mixture containing said desorbent and para-cresol; and (d) separating para-cresol from said mixture.

11. The process of claim 10 wherein said aliphatic alcohol is a straight-chain aliphatic alcohol of $C_4$ to $C_6$.

12. The process as defined in claim 10 wherein said aliphatic ketone is diethyl ketone and said aliphatic alcohol is n-butyl alcohol.

* * * * *